United States Patent [19]

Mattox

[11] Patent Number: 5,127,934
[45] Date of Patent: Jul. 7, 1992

[54] STABILIZED COMPOSITIONS COMPRISING ISOTHIAZOLONES AND EPOXIDES

[75] Inventor: John R. Mattox, Perkasie, Pa.

[73] Assignee: Rohm and Haas Company, Philadelphia, Pa.

[21] Appl. No.: 476,147

[22] Filed: Feb. 7, 1990

Related U.S. Application Data

[63] Continuation of Ser. No. 194,234, May 16, 1988, abandoned.

[51] Int. Cl.$^5$ ............................................. A01N 43/80
[52] U.S. Cl. ........................................ 71/67; 514/372; 548/213
[58] Field of Search ................... 548/213; 514/372; 71/67

[56] References Cited

U.S. PATENT DOCUMENTS

| | | | |
|---|---|---|---|
| 3,523,121 | 8/1970 | Lewis et al. | 548/213 |
| 3,755,224 | 8/1973 | Lutz | 252/182 X |
| 3,761,488 | 9/1973 | Lewis et al. | 548/213 |
| 3,870,795 | 3/1975 | Miller et al. | 514/372 |
| 4,067,878 | 1/1978 | Miller et al. | 548/213 |
| 4,129,448 | 12/1978 | Greenfield et al. | 106/15 R |
| 4,163,795 | 8/1979 | Burk et al. | 514/528 |
| 4,163,798 | 8/1979 | Burk et al. | 514/528 |
| 4,165,318 | 8/1979 | Greenfield et al. | 548/213 |
| 4,190,668 | 7/1980 | Burk et al. | 514/528 |
| 4,241,080 | 12/1980 | Burk et al. | 514/528 |
| 4,276,211 | 6/1981 | Singer | 106/18.32 X |
| 4,281,014 | 7/1981 | Yaffe | 514/372 |
| 4,424,386 | 1/1984 | Ishibe | 570/109 |
| 4,906,274 | 3/1990 | Mattox | 71/67 |
| 4,920,137 | 4/1990 | Segall et al. | 514/372 |

FOREIGN PATENT DOCUMENTS

| | | |
|---|---|---|
| 194146 | 9/1986 | European Pat. Off. |
| 2411764 | 9/1974 | Fed. Rep. of Germany |
| 1318306 | 5/1986 | Japan |

*Primary Examiner*—Diana G. Rivers
*Attorney, Agent, or Firm*—Michael B. Fein

[57] ABSTRACT

Organic stabilizers are used to stabilize various materials which are normally unstable neat or in solution. These compositions exhibit bactericidal, fungicidal and algaecidal properties.

19 Claims, No Drawings

STABILIZED COMPOSITIONS COMPRISING ISOTHIAZOLONES AND EPOXIDES

This application is a continuation of application Ser. No. 194,234, filed May 16, 1988, now abandoned.

This invention relates to stable compositions of 3-isothiazolones, their preparation, and their use in controlling living organisms. The isothiazolones which are stabilized include those disclosed in U.S. Pat. Nos. 3,523,121 and 3,761,488 as represented by the following structural formula:

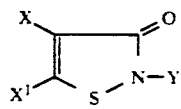

wherein

Y is an unsubstituted or substituted alkyl of from 1 to 18 carbon atoms, an unsubstituted or halo substituted alkenyl or alkynyl of from 2 to 8 carbon atoms, and, preferably, from 2 to 4 carbon atoms, an unsubstituted or substituted cycloalkyl of from 5 to 8 carbon atoms, an unsubstituted or substituted aralkyl or an unsubstituted or substituted aryl;

X is hydrogen, halo, or a (C1-C4)alkyl and $X^1$ is hydrogen, halo or (C1-C4)alkyl.

U.S. Pat. Nos. 3,523,121 (column 1, lines 40-64 and column 2, lines 1-21) and 3,761,488 (column 1, lines 25-61) fully describe the substituents on the isothiazolone ring in terms of type and carbon content, and are incorporated herein by reference.

Representative Y substituents include methyl, ethyl, propyl, isopropyl, butyl, hexyl, octyl, cyclohexyl, benzyl, 3,4-dichlorobenzyl, 4-methoxybenzyl, 4-chlorobenzyl, 3,4-dichlorophenyl, 4-methoxyphenyl, hydroxymethyl, chloromethyl, chloropropyl and the like.

Preferred isothiazolones are 5-chloro-2-methyl-3-isothiazolone, 2-methyl-3-isothiazolone,2-octyl-3-isothiazolone, 4,5-dichloro-2-cyclohexyl-3-isothiazolone and 4,5-dichloro-2-octyl-3-isothiazolone.

Japanese Patent 12243/83 discloses stabilizing a mixture of an isothiazolone and 2-hydroxymethyl-2-nitro-1,3-propanediol with a diol solvent. However, 2-hydroxymethyl-2-nitro-1,3-propanediol is a formaldehyde releaser, which is known to stabilize isothiazolones (see U.S. Pat. Nos. 4,165,318 and 4,129,448).

European Patent Application 194,146 discloses stabilizing isothiazolones in non-aqueous, salt-free systems by several hydroxylic solvents, including dipropylene glycol.

U.S. Pat. No. 3,755,224 discloses isothiazolones as stabilizers for poly(vinyl chloride) by blending an isothiazolone with a plasticizer such as epoxidized soybean oil.

There is no teaching of stabilization of the isothiazolone under these mixing/processing conditions. Combinations of thiazolidines (having a saturated five-membered ring with adjacent sulfur and nitrogen atoms) with nitroalkanes are taught in U.S. Pat. No. 4,424,386 in combination with certain organic compounds, including epoxides, in inhibition of metal corrosion in degreasing of aluminum.

There is no suggestion of stabilization of the thiazolidine per se, and no reference to the present unsaturated isothiazolones.

The following references are noted as showing stabilization of certain classes of biologically active compounds, but not isothiazolones, with chemicals related to those of the present invention. U.S. Pat. No. 4,276,211 teaches stabilization against color instability of iodoalkynl-N-hydrocarbylcarbamates with organic epoxy compounds.

German Application 2411764 teaches stabilization of an acid-labile quinoxalinylthionophosphate with epoxycyclohexane.

A series of patents to Burk et al. teaches stabilization of halogenated amide antimicrobials, such as 2,2-dibromonitrilopropionamide, usually in the presence of some water, with a variety of organic stabilizers. U.S. Pat. No. 4,190,668 teaches cyclic ethers. There is no suggestion that any of these stabilizers would be useful in the neat or non-aqueous stabilization of isothiazolones.

Thus, until now means for stabilization of isothiazolones against thermal degradation or storage degradation has generally been by metal salts, formaldehyde or formaldehyde releasers.

Both formaldehyde or formaldehyde-releasers and salt stabilization of isothiazolones have some drawbacks. Formaldehyde is a suspected carcinogen, and it is desirable not to use formaldehyde in applications where contact with human skin or lungs may occur.

This invention is directed to stable biocidal isothiazolone compositions in which (1) water is substantially eliminated, (2) salt neutralization is eliminated and (3) the need for nitrate stabilizer salts is substantially eliminated.

The epoxides (II) useful in this invention have the following structural formula:

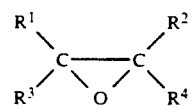

wherein $R^1$ is hydrogen, alkoxyalkyl, for example lower alkoxy lower alkyl wherein "lower" means containing from 1 to 6 carbon atoms such as methoxymethyl, ethoxymethyl, propoxyethyl, n-butoxyethyl, tert-butoxymethyl, tert butoxybutyl and the like, 2,3-epoxy dialkoxy alkyl, for example 2,3-epoxy di-lower alkoxy lower alkyl such as 2,3-epoxy-1-propoxyethoxymethyl, 2,3-epoxy-1-butoxyethoxyethyl and the like;

$R^1$ may also be a radical of the formula:

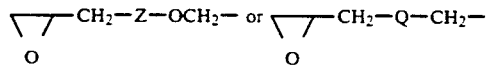

wherein Z is straight or branched chain lower alkylene or halo substituted lower alkylene of from 2 to 6 carbon atoms for example ethylene, propylene, butylene, pentylene, hexylene, 1-methyl propylene, 2,2-dimethyl propylene, 2,2-dibromomethyl propylene, 2,2-dichloromethyl propylene and the like; Q is ($C_1$-$C_4$)alkylene or carbonylarylcarboxy such as carbonylphenylcarboxy and the like;

$R^2$ is hydrogen or $R^1$ and $R^2$ or $R^1$ and $R^3$ may be joined, together with the carbon to which they are attached, to form an alkylene chain of from 3 to 7 carbon atoms, for example propylene, butylene, pentylene, hexylene, heptylene and the like which alkylene chain may be substituted with a lower alkylene to form a bicyclo alkane for example, bicyclo [3.1.1] heptane,bicyclo [2.2.2.]octane and the like, or substituted with a lower alkenyl radical such as ethenyl, 1-methylethenyl, butenyl and the like;

$R^3$ is hydrogen or lower alkyl such as methyl, ethyl, propyl, butyl, pentyl and the like; and $R^4$ is hydrogen.

Preferred epoxy compounds (IIa) are those having the following structural formula:

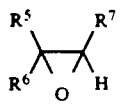     IIa wherein $R^5$ is hydrogen, lower alkoxy, lower alkyl, or 2,3-epoxy-1-propoxyethoxymethyl (i.e.

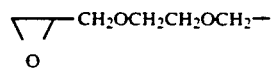

$R^6$ is hydrogen or lower alkyl, $R^7$ is hydrogen, or $R^5$ and $R^7$ or $R^5$ and $R^6$ may be joined together with the carbon atom to which they are attached to form an alkylene chain of from 3 to 7 carbon atoms, which alkylene chain may be substituted with a lower alkylene to form a bicycloalkane (i.e. —CH$_2$CH$_2$CH$_2$CH$_2$—);

Examples of epoxy compounds which may be employed include those of the following formula:

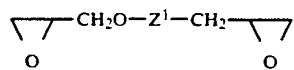     IIb wherein $Z^1$ is —(CH$_2$CH$_2$O)$_{\overline{n}}$, (CH(CH$_3$)CH$_2$O), —(CH$_2$—CH(OH)CH$_2$)$_{\overline{n}}$, —(CH$_2$—C(CH$_3$)$_2$CH$_2$)$_{\overline{n}}$ or —(CH$_2$)$_{\overline{n}}$ and n is an integer of from 0 to 6.

This invention comprises a stable biocidal composition which contains from about 0.1 to about 99.9 parts of one or more isothiazolones and an effective stabilizing amount of an epoxide of Formula II (supra), preferably, an epoxide in the range of from 0.1 to about 99.9 percent.

More preferably, the composition comprises at least one isothiazolone wherein Y is C$_1$–C18, alkyl or phenyl or C$_3$—C$_{12}$, cycloalkyl; X is hydrogen or halo; and $X^1$ is hydrogen or halo. Typical formulation ranges are illustrated in the following Table (all percentages are parts by weight) for both a concentrated solution of the isothiazolone and a dilute solution. A preferred composition comprises from 1 to 50 parts of the isothiazolone and from 1 to 25 parts of the epoxide. A more preferred composition comprises from 1 to 25 parts of the isothiazolone and from 1 to 10 parts of the epoxide. For certain uses, such as shipping of large quantities, more concentrated solutions may also be utilized.

| FORMULATIONS TABLE | | |
|---|---|---|
| Isothiazolone (I. Supra) | Epoxide (II. supra) | Solvent |
| 0.1 to 99.9% | 0.1% to 99.9% Preferred | 0 to 99.8% |
| 1 to 50% | 1 to 25% More Preferred | 25 to 98% |

| -continued | | |
|---|---|---|
| FORMULATIONS TABLE | | |
| Isothiazolone (I. Supra) | Epoxide (II. supra) | Solvent |
| 1 to 25% | 1 to 10% | 65 to 98% |

When it is desired to package the isothiazolone with only the stabilizer and no other organic solvent or water present the amount of stabilizer or mixture of stabilizers employed will be from about 1 percent to about 25 percent. The isothiazolone may be present in a bulk form or packaged or encapsulated in some manner, including a form for controlled release. The ratio of epoxide to isothiazolone is preferably from about 1:7 to about 1.5:1.

Epoxides, also known as oxiranes, are three-membered cyclic ethers. They are a well-known class of organic compounds, many of which are commercially available. Among such are alkylene oxides, formed by the epoxidation of olefins, both terminally and internally unsaturated, including cyclic olefins where the double bond is either internal or external to the ring. Another well-known class are those epoxides formed by the dehydration of 1,2-glycols; among such are glycidyl ethers derived from alpha-ethers of glycerol.

Preparative methods are well-known; they include:

a) olefin oxidation by organic peroxides, such as performic acid, peracetic acid, metachloroperbenzoic acid, and the like. This reaction is broadly useful with a wide variety of olefins;

b) oxidation of olefinic double bonds with alkaline hydrogen peroxide;

c) direct oxygen addition to olefins;

d) cyclodehydrohalogenation of halohydrins of the structure

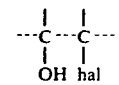

Such halohydrins may be formed by the addition of hypohalous acids across the double bond.

e) a similar reaction where hal is replaced by OSO$_2$R$^6$ where R$^6$ is methyl, p-tolyl, phenyl, trifluoromethyl and the like.

f) the Darzens condensation of aromatic aldehydes and alpha-chloroesters catalyzed by sodium to form an alpha-aryl-beta-carbalkoxyoxirane. A broad variety of epoxides, including di- and polyepoxides and epoxides pendant to oligomeric or polymeric structures, will be useful in stabilization of isothiazolones. Low molecular weight volatile epoxides, such as ethylene oxide or propylene oxide are less preferred because of their volatility.

Examples of epoxides believed useful in the stabilization of isothiazolones include: 1,2-cyclohexene oxide, 1,2-epoxyoctane, 2,3-epoxyhexane; beta-pinene oxide; phenyl glycidyl ether, n-butyl glycidyl ether, tert-butyl glycidyl ether, p-tert-butylphenyl glycidyl ether, benzyl 3,4-epoxybutyl ether, n-butyl glycidyl thioether; ethylene glycol bis(glycidyl ether), poly(ethylene glycol)$_2$ bis(glycidyl ether), poly(ethylene glycol)$_9$ bis(glycidyl ether), hexylene glycol bis(glycidyl ether); phenyl poly(ethyleneoxy)5 glycidyl ether, propylene glycol bis(glycidyl ether), poly(propylene glycol)$_2$ bis(- glycidyl ether), poly(propylene glycol)₃ bis(glycidyl ether), poly(propylene glycol)₁₁ bis(glycidyl ether), neopentyl glycol bis(glycidyl ether), dibromoneopentyl glycol bis(glycidyl ether), o-phthalic acid bis(glycidyl ester), sorbitol polyglycidyl ether (average degree of etherification is about 4); polyglycerol poly(glycidyl ether) (average degree of etherification per glycerol unit=1; average degree of polymerization of glycerol is between 3 and 4), diglycerol polyglycidyl ether, glycerol di(glycidyl ether) glycerol, tri(glycidyl ether), trimethylolpropane tri(glycidyl ether).

In addition, the following epoxides may be employed to those listed above: ethylene oxide, propylene oxide, 1,2-epoxybutane, 2,3-epoxybutane, 1,2-epoxyoctane, 9,10-epoxy-5,6-octadecene, 3,4-epoxyoctane, 1,2-epoxy-3-methylbutane, 2,3-epoxy-4-methylpentane, 3,4-epoxydodecane, cyclopentene oxide, 1,2-epoxy-4-ethylcyclohexane, cyclooctene oxide, alpha-pinene oxide, beta-pinene oxide, 2,3-epoxybicycloheptane (2.2.1), 3,4-epoxybutanol-1, 3,4-epoxybutanol-1 acetate, 9,10-epoxystearic acid, methyl 9,10-epoxystearate, glycerol tris(9,10-epoxystearate), 3,4-epoxybutanol-1 9,10-epoxystearate, 5,6,9,10-diepoxystearic acid, butyl 5,6,9,10-diepoxystearate, 2,3-epoxybicycloheptyl(2.2.1)-5-ethanol, bis(2,3-epoxypropyl o-phthalate, 2,3-epoxybicycloheptyl(2.2.1)-5-ethanol 2,3-epoxybutanoate, 2,3-epoxypentanol-1 5,6-dodecene-1-carboxylate, 9,10-epoxy-5,6-octadecenol-1, N,N-dimethyl 9,10-epoxystearamide, N-methyl-N-2,3-epoxypropyl acetamide, N,N-di(2,3-epoxypropyl) 2,3-epoxybutanoate, and the like; digycidyl ether (di(2,3-epoxy-1-propyl) ether), allyl glycidyl ether, ethyl 9,10-epoxy-1-octadecanol ether, allyl 3,4-epoxy-5-methyl-2-hexyl ether, phenyl glycidyl ether, benzyl (epoxybicycloheptyl)methyl ether, dibromoneopentyl glycol bis (3,4-epoxyoctanol-1) ether, phenylpoly (ethyleneoxy) 9,10-epoxydodecanol-1 ether, and the like.

It is preferred that the epoxide be relatively accessible, such as within a cyclic ring or of the structure

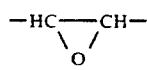

It is especially preferred that the functionality be at a terminal point of the molecule, i.e.

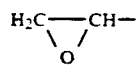

Very low molecular weight epoxides, such as ethylene oxide and propylene oxide, are less preferred because of their volatility. Especially preferred are cyclohexene oxide, phenyl-glycidyl ether, alpha-pinene oxide, beta-pinene oxide, isopropylglycidyl ether, tert-butylglycidyl ether, n-butylglycidyl ether and the bisglycidyl ethers of ethylene and diethylene glycols.

Solvents other than epoxides may be used to dissolve the isothiazolones and may be any organic solvent which dissolves the isothiazolones, are compatible with the proposed end use, do not destabilize the isothiazolone, and do not react with the epoxide to eliminate its stabilizing action.

Hydroxylic solvents, for example, polyols, such as glycols, alcohols and the like, may be used. Under conditions of high dilution and high ratios of stabilizer to isothiazolone, glycols may be successfully used. In certain formulations, hydrocarbons, either aliphatic or aromatic, are useful solvents.

Preferred solvents are capped polyols, wherein the free hydroxy is replaced with an ether or ester function. Especially preferred are 2,5,8,11-tetraoxadocecane, commonly known as triethylene glycol dimethyl ether or euglyme, and 4,7-dioxaundecanol-1 acetate, commonly known as diethylene glycol butyl ether acetate.

The amounts of epoxide employed will vary depending on use conditions and concentrations of the isothiazolone in the mixture. In more concentrated solutions, effective amounts of epoxide based on isothiazolone are in the ratios of from about 1:4 to about 1:2. Obviously higher amounts may be used, but at additional cost. At low levels of dilution of the isothiazolone (such as from 1 to 2 percent isothiazolone in the solvent), the ratio of stabilizer to isothiazolone can range from about 1:7 to about 2:1.

This invention permits the stabilization of isothiazolones wherein the previously necessary stabilization salts are substantially reduced and even eliminated. Useful stabilization salts which can be employed are those disclosed in U.S. Pat. Nos. 3,870,795 and 4,067,878 and include stabilization salts selected from:

1) Metal nitrates, where the metal is barium, cadmium, calcium, chromium, cobalt, copper, iron, lead, lithium, magnesium, manganese, mercury, nickel, sodium, silver, strontium, tin, zinc and the like; and 2) Copper (2+) salts where the anion is halide, sulfate, nitrate, nitrite, acetate, chlorate, perchlorate, bisulfate, bicarbonate, oxalate, maleate, carbonate, or phosphate and the like.

Uses of these new organically stabilized biocides are typically at any locus subject to contamination by bacteria, fungi or algae. Typically loci are in aqueous systems such as water cooling, laundry wash water, oil systems such as cutting oils, oil fields and the like where microorganisms need to be killed or where their growth needs to be controlled.

The stabilized biocide compositions of this invention are advantageous over salt stabilized isothiazolones described in the art and are the biocides of choice where salts pose a problem.

For example, certain emulsions upon the addition of a salt may coagulate. The compositions of this invention avoid this problem and therefore can be used in emulsions such as photographic emulsions, coating emulsions, (e.g. paints) to form solid protective or decorative films; electronic circuitry, wood, metals, plastics, fibers, membranes, carpet backings, ceramics and the like where surfaces need to be coated or protected, adhesives, caulks, and sensitive emulsions.

In many salt stabilized biocide systems of the prior art there is a potential for solids formation caused by interactions with other salts in the system, interaction with certain salt forming organics, by the conversion to organic salts, or simply by incompatibility with the system. The stabilized biocide compositions of this invention would be preferred in those systems. Also, the compositions of this invention are useful in fuel systems such as diesel fuel, gasoline, kerosene, certain alcohols, and the like, because they eliminate the possibility of salt deposits on component parts. Another reason for eliminating salts is to avoid an environment in which corrosion can occur. For example, chloride salts (among others) have a corrosive effect on many metals and are to be avoided where possible. In water treatment systems where low cation and anion levels are important, this is especially true. Those familiar with the art in various areas where biological growth needs to be controlled will quickly recognize those applications where significant reduction of or elimination of salts will be desired. In many cases it is necessary to eliminate interactions between the stabilizing salts and other components of the system or formulation components which otherwise could reduce the performance or value of such systems.

It is also recognized that the isothiazolone stabilizers of this invention have other applications known to those skilled in the art. For example, epoxides are known to serve as reactive scavengers for molecules containing —OH, $NH_2$, —SH and other nucleophilic groups. A biocide formulation stabilized with an epoxide would be particularly advantageous where the dual function of biocidal/biostatic activity and scavenging would lead to advantageous results.

Because isothiazolone biocides are so active, the low level required to achieve stabilization also makes them ideal when compared to many known biocides because at the low levels required they are not likely to interfere with other components in systems requiring protection or with systems upon which the protected systems will be applied.

Potential areas of general application include disinfectants, sanitizers, cleaners, deodorizers, liquid and powder soaps, skin removers, oil and grease removers, food processing chemicals, dairy chemicals, food preservatives, animal food preservatives, wood preservation, paint, lazures, stains, mildewcides, hospital and medical antiseptics, medical devices, metal working fluids, cooling water, air washers, petroleum production, paper treatment, paper mill slimicides, petroleum products, adhesives, textiles, pigment slurries, latexes, leather and hide treatment, petroleum fuel, laundry sanitizers, agricultural formulations, inks, mining, nonwoven fabrics, petroleum storage, rubber, sugar processing, tobacco, swimming pools, photographic rinses, cosmetics, toiletries, pharmaceuticals, chemical toilets, household laundry products, diesel fuel additives, waxes and polishes and many other applications where water and organic materials come in contact under conditions which allow the growth of undesired microorganisms.

In the stabilization of plastic articles, it is desirable to eliminate salts in the isothiazolones, as salts may contribute to deterioration of optical properties and/or increase water pickup and haze levels.

In some cosmetic formulations, it is also important to have low water and salt content. Eliminating nitrate salts avoids the possibility of nitrosamine formation with any amines present in the formulation. Removal of multivalent cations from the biocide may also eliminate the known possibility of creating physical incompatibility problems in certain cosmetic formulations caused by precipitation of salts or complexes.

It is well known in the art that the performance of biocides is frequently enhanced by combining with one or more other biocides. In fact, there have been numerous examples of synergistic combinations of biocides. Thus, other known biocides may be combined advantageously with the stabilized isothiazolones of this invention.

Isothiazolones are used as disinfectants, in oil field water treatment, as watercooling system microbiocides, as preservatives for aqueous dispersions or organic polymers, as wood pulp white water slimicides, as cosmetic preservatives, as cutting oil, jet fuel, and heating oil preservatives, and the like. Solutions of isothiazolones are also applied to a solid substrate, such as fabric, leather, or wood, as a preservative, or admixed with plastics.

The products of this invention are especially useful as preservatives for the following:
1. Cosmetics, as it eliminates or substantially reduces the presence of nitrates which under certain conditions in the presence of amines or amine precursors may lead to the formation of nitrosoamines.
2. Oils and fuels, since added salts and moisture are eliminated or minimized thus preventing potential corrosion, deposition or sludge formation.
3. Emulsions and dispersions that are sensitive to divalent cations are those contained in a wide variety of products, such as paints, cosmetics, floor polishes and binders.
4. Plastics, as it eliminates or substantially reduces precipitated salts which can contribute directly or indirectly to haze, opacity, or physical weakness in the surface.

The following examples will further illustrate this invention, but are not intended to limit it in any way. All parts and percentages are by weight and all temperatures in degrees Centigrade, unless otherwise stated.

For comparison of the stabilization of the compositions of this invention with known materials the following tests were employed: using a thermally-controlled solid metal block with bored holes as receptacles for the vials and with demonstrated temperature control, vials of stabilizer, solvent, and isothiazolone were made up and heated for fixed periods of time. The percentage of the starting isothiazolone remaining was determined high performance liquid chromatography (HPLC). Temperatures of 40°, 55°, and 70° C. were used. Results were considered indicative of acceptable stability when remainder values indicated essentially no loss during the time specified for the isothiazolone or isothiazolone mixture studied.

EXAMPLES 1-6

I. Stability Test for 5-Chloro-2-methylisothiazolin-3-one/2-Methylisothiazolin-3-one A 3:1 mixture of 5-chloro-2-methylisothiazolin-3-one/2-methylisothiazolin-3-one (16.2%) is mixed at 14% active ingredient (AI) in triglyme (76.8%) with the chosen stabilizer (7%). The amount of AI remaining is measured after four weeks at 40° C. and after one and two weeks at 70° C. HPLC is used to measure AI. Maintenance of AI must be >85% to meet the target of most preferred. Other stabilizers may be less effective in the test, but may be adequate for stabilization under shorter time, less exacerbated conditions. This epoxide stabilized material is compared with a 3:1 mixture of 5-chloro-2-methylisothiazolin-3-one/2-methylisothiazolin-3-one stabilized with magnesium nitrate (15%).

The following results were obtained.

| Ex. No. | Stabilizer | 1 week, 70° | 2 weeks, 70° | 4 weeks, 40° |
|---|---|---|---|---|
| 1 | None | F | F | 32 |
| 2 | $Mg(NO_3)_2$ 15% | P | P | P |
| 3 | beta-Pinene oxide | P | 80 | P |
| 4 | tert-Butyl glycidyl ether | P | P | P |

-continued

| Ex. No. | Stabilizer | 1 week. 70° | 2 weeks. 70° | 4 weeks. 40° |
|---|---|---|---|---|
| 5 | Ethylene glycol bis-glycidyl ether | P | P | P |
| 6 | Diethylene glycol bis-glycidyl ether | P | 80 | P |

(P indicates that more than 85% of AI has been retained
F indicates less than 10% retention, ie. complete and unacceptable loss of activity.)

EXAMPLE 7

Shown below is the percent of 5-chloro-2-methyl isothiazolin-3-one stabilized with n-butyl glycidyl ether in various solvents remaining after 2 weeks at 70° C., where initial isothiazolone content was 14% and 7% stabilizer is used, the balance being the solvents listed. The second line is the control with no stabilizer.

| Tetra-Glyme | Dipropylene Glycol | Propylene Glycol Methyl Ether Acetate | Diethylene Glycol Butyl Ether Acetate | Triacetin (Glyceryl Triacetate) | Ethylene Glycol Diacetate | DPG +5% $H_2O$ |
|---|---|---|---|---|---|---|
| 99 | 67 | 98 | 100 | 98 | 97 | 0 |
| 0 | 0 | 0 | 17 | 21 | 0 | |

EXAMPLE 8

Stabilization of Neat Mixture of 3:1 2-Methyl-5-chloroisothiazolone and 2-Methylisothiazolone The neat isothiazolone was stabilized with 5% or 20% butanediol bis(glycidyl ether). Mixtures were stored one week at 40° and 55° and compared with unstabilized neat isothiazolone. The retention of active ingredient is shown below:

| Stabilizer (S) | % S | One week. 40° | One week. 55° |
|---|---|---|---|
| (Control) | — | 98.4% | 49.7% |
| Butanediol bisglycidyl ether | 5 | 100.0% | 47.0% |
| Butanediol bisglycidyl ether | 20 | 95.4% | 98.9% |

EXAMPLE 9

Ratios of Stabilizer to isothiazolone at 14% AI

Data is presented for weeks of stability at 55°. AI was 14% of the mixed isothiazolone, the stabilizer was at percentages of 0 to 7, and the remainder was the solvent. BCA = diethyleneglycol butyl ether acetate; PGE = phenyl glycidylether. (P means retention of greater than 85% activity.) Some stability is offered by the solvent alone.

| | | % AI Remaining After | | |
|---|---|---|---|---|
| Stabilizer, % | Solvent | 2 weeks | 4 weeks | 8 weeks |
| PGE 7 | BCA | P | P | P |
| PGE 5 | | P | P | P |
| PGE 3 | | P | P | P |
| PGE 1 | | P | P | 25 |
| | | 55 | 30 | 20 |

EXAMPLE 10

Hair Shampoo

A solution containing 1.5% of N-methyl-5-chloroisothiazolin-3-one and N-methylisothiazolin-3-one (approximately 3:1 mixture) and 2.0% of ethylene glycol bis(glycidyl ether) stabilizer in 96.5% dipropylene glycol is used as a preservative for a hair shampoo.

EXAMPLE 11

Elimination of Salt Shock in Emulsions

Salt shock is observed as a precipitate or gelatinous mass that forms in the polymer emulsion when isothiazolone, containing divalent metal ions (e.g. $Mg++$, $Cu++$), is added as a preservative. The polymer emulsion is initially passed through a 325 mesh screen to remove any gel that might be present from manufacture. Isothiazolone is added to a total amount of 30 ppm AI based on total polymer emulsion. A 250g. emulsion sample in a pint container is used. The sample is gently swirled after pipetting the appropriate amount of isothiazolone. The sample is inverted twice to mix and allowed to stand at ambient temperature for sixty minutes. The sample is again passed through a 325 mesh screen. Any gel or precipitate on the screen is washed with deionized water to remove residual, uncoagulated polymer emulsion. The material remaining on the screen is collected and dried overnight at 50° C. This is followed by heating 1 hour at 150° C. to remove any remaining water. The residue is then weighed. The amount of butanediol bis(glycidyl ether) stabilizer is equivalent to the isothiazolone, and the solvent is diethyleneglycol butyl ether acetate.

The small amount of gel formed when the emulsion is preserved with salt-free epoxide-stabilized isothiazolone will not be detrimental in the use of the emulsion in various applications such as paints, caulks, and the like. The amount of gel formed when salt-stabilized isothiazolone is used as a preservative would be easily visible and objectionable.

EXAMPLE 12

Microbial Speed-of-Kill

The following test, when carried out to determine the microbial speed of kill of an epoxide stabilized isothiazolone compared to the nitrate stabilized isothiazolone, will illustrate equivalent bactericidal activity when either the nitrate or epoxide stabilizer is used.

The speed-of-kill test measures bactericidal activity in water free of organic matter. It measures the loss of cell viability in an aqueous suspension of bacterial cells as a function of time when these cells are contacted with a defined concentration of test compound in the water. This is done by taking aliquots of the cell suspensions at the appropriate time interval and assaying the number of viable cells per milliliter by plate count or most probable number (MPN) methodology. These measurements are done on the cell suspensions containing no test compound. The viable cell counts of the test and control samples are then compared to determine cell death.

The inoculum is prepared by growing the bacteria on a slant for 24 hours and then harvesting the cells into phosphate buffer. To start the test at zero time, one volume of bacterial inoculum is added to 100 volumes of test solution containing compound at the final test concentration. At appropriate time intervals, such as 2, 4 and/or 24 hours, aliquots of all the test samples and controls are assayed for viable cell count, reported as most probable number (MPN) per ml.

In this test, addition of epoxide stabilizer will not diminish the efficacy of a freshly prepared solution of a metal-salt-free isothiazolone in an organic solvent at either relatively high (14% AI) or relatively low (1.5%) isothiazolone concentrations. Comparisons are made against the unstabilized solution and against a metal-salt stabilized aqueous solution at the same AI level.

EXAMPLE 13

Minimum Inhibitory Content Testing

A minimum inhibitory concentration (MIC) test is used to evaluate the antimicrobial activity of a test compound in preservative applications. The MIC value is obtained in the following manner. A volume of the stock solution containing 1% AI is dispensed into enrichment broth to give an initial starting test concentration of 250 ppm compound. At the start of the test, each vessel in the dilution series, except the first vessel, contains an equal volume of the compound free broth. The first vessel contains twice the volume of broth with the starting concentration of test compound. One half of the broth from the first vessel is transferred to the second vessel. After being mixed, one half the resulting volume is removed from the second vessel and transferred to the third vessel. The entire cycle is repeated 8 to 12 times, depending on the number of dilutions desired. The result is a two-fold serial dilution of test compound in the enrichment broth.

Each vessel is then inoculated with a cell suspension of the appropriate test organism. Bacteria are grown in broth and fungi on agar slants, for a time and at a temperature appropriate to the species being tested. At the end of the growth period, the broth is vortexed to disperse the cells. In the case of fungi, the spores are harvested by pipetting water onto the slant and dislodging the spores with a sterile loop. The cell/spore suspensions are standardized by controlling incubation time and temperature and the volume of the diluent. Once inoculated, the vessels are incubated at the appropriate temperature, and then examined for growth/no growth. The minimum inhibitory concentration (MIC) is defined as the lowest concentration of compound that results in complete inhibition of growth of the test organism.

In this test, typical values for water-based salt stabilized systems are shown below.

| Microorganism: | System I | System II |
| --- | --- | --- |
| Psfl = Pseudomonas fluorescens | 2 | 2 |
| Psal = Pseudomonas aeruginosa | 4 | 4 |
| Saur = Staphylococcus aureus | 16 | 16 |
| Ecol = Escherichia coli | 8 | 4 |
| Calb = Candida albicans | 2 | 2 |
| Anig = Aspergillus niger | 2 | 2 |
| Apul = Aureobasidium pullulans | 1 | 2/1 |

Values for freshly-prepared salt-free solutions at similar AI levels will be approximately those shown above, and those values will be essentially unaffected by presence of epoxide stabilizers of the present invention at use levels (relative to the AI concentration chosen) taught herein. Useful formulations are: 1.5% AI, 2% t-butyl glycidyl ether, 96.5% dipropylene glycol or 14% AI, 9% poly(propylene) glycol (n=2) bis(glycidyl ether), 77% diethyleneglycol butyl ether acetate.

What is claimed is:

1. A stabilized composition comprising a compound of the formula:

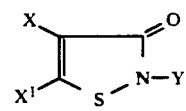

wherein Y is alkyl from 1 to 18 carbon atoms, alkenyl or alkynyl of 2 to 8 carbon atoms, a cycloalkyl of from 5 to 8 carbon atoms, aralkyl, or aryl, and X and X are hydrogen, halogen, or a ($C_1$-$C_4$)alkyl and an effective amount of an epoxide of the formula:

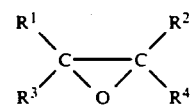

wherein $R^1$ is hydrogen, alkoxyalkyl, 2,3-epoxy dialkoxyalkyl; $R^1$ may also be a radical of the formula:

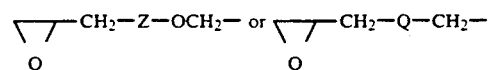

wherein Z is straight or branched chain lower alkylene or halo substituted lower alkylene of from 2 to 6 carbon atoms; Q is a ($C_1$-$C_4$)alkylene or carbonylphenylcarboxy; $R^2$ is hydrogen or $R^1$ and $R^2$ or $R^1$ and $R^3$ may be joined together with the carbon atoms to which they are attached to form an alkylene chain of from 3 to 7 carbon atoms, which alkylene chain may be substituted with a lower alkylene to form a bicycloalkane, or substituted with a lower alkenyl radical; $R^3$ is hydrogen or lower alkyl and $R^4$ is hydrogen.

2. The composition of claim 1 which comprises from 0.1 to 99.9 parts of one or more compounds of the formula:

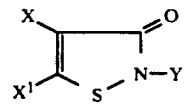

wherein X, $X^1$ and Y are as defined in claim 1 and from 0.1 to 99.9 parts of the epoxide of claim 1.

3. The composition of claim 2 which comprises from 1 to 50 parts of the isothiazolone and from 1 to 25 parts of the epoxide.

4. The composition of claim 3 which comprises from 1 to 25 parts of the isothiazolone and from 1 to 10 parts of the epoxide.

5. The composition of claim 4 comprising the isothiazolone of claim 4 wherein Y is ($C_1$-$C_{18}$)alkyl or ($C_3$-$C_{12}$)cycloalkyl; X is hydrogen or halo and $X_1$ is hydrogen or halo, and an epoxy compound of the following structural formula:

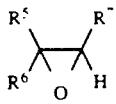

wherein $R^5$ is hydrogen, lower alkoxy, lower alkyl, or 2,3-epoxy-1-propoxyethoxymethyl; $R^6$ is hydrogen or lower alkyl; $R^7$ is hydrogen or $R^5$ and $R^6$ or $R^5$ and $R^7$ may be joined together with the carbon atom to which they are attached to form an alkylene chain of from 3 to 7 carbon atoms, which alkylene chain may be substituted with a lower alkylene to form a bicycloalkane.

6. The composition of claim 5 which comprises about 14 parts of an isothiazolone selected from 5-chloro-2-methyl-3-isothiazolone, 2-methyl-3-isothiazolone, 2-octyl-3-isothiazolone, or 4,5-dichloro-2-octyl-3-isothiazolone.

7. The composition of claim 5 which comprises about 1.5 parts of an isothiazolone selected from 5-chloro-2-methyl-3-isothiazolone, 2-methyl-3-isothiazolone, 2-octyl-3-isothiazolone, or 4,5-dichloro-2-octyl-3-isothiazolone.

8. The composition of claim 6 or 7 which comprises an epoxide selected from alpha-pinene oxide, beta-pinene oxide, cyclohexene oxide, tert-butyl glycidyl ether, isopropyl glycidyl ether, the bis(glycidyl ether) of ethylene glycol, the bis(glycidyl ether) of diethylene glycol, and the bis(glycidyl ether) of 1,4-butanediol.

9. A method of inhibiting the growth of bacteria, fungi, or algae in a locus subject to contamination by bacteria, fungi, or algae, which comprises incorporating onto or into the locus, in an amount which is effective to adversely affect the growth of bacteria, fungi, or algae, the composition of claim 1.

10. The method of claim 9 wherein the locus is an aqueous medium.

11. The method of claim 9 wherein the locus is a cutting oil formulation.

12. The method of claim 9 wherein the locus is a water-cooling system.

13. The method of claim 9 wherein the locus is a solid protective or decorative film.

14. The method of claim 9 wherein the locus is fabric, leather, paper, or wood.

15. The method of claim 9 wherein the locus is laundry wash water.

16. The method of claim 9 wherein the locus is a cosmetic formulation.

17. The method of claim 9 wherein the locus is a fuel system.

18. The method of claim 9 wherein the locus is plastic.

19. The method of claim 9 wherein the locus is an emulsion.